United States Patent [19]

Springer et al.

[11] 4,309,897
[45] Jan. 12, 1982

[54] EXHAUST GAS SENSOR SEAL AND PROTECTION TUBE ARRANGEMENT

[75] Inventors: Jerry L. Springer; Charles M. Wells, both of Livonia, Mich.

[73] Assignee: Ford Motor Company, Dearborn, Mich.

[21] Appl. No.: 166,729

[22] Filed: Jul. 7, 1980

Related U.S. Application Data

[63] Continuation of Ser. No. 5,423, Jan. 22, 1979, abandoned.

[51] Int. Cl.³ ............................................. G01N 27/12
[52] U.S. Cl. .......................................... 73/23; 338/34
[58] Field of Search .................... 73/23, 27 R; 338/34; 422/98; 204/195 S; 277/178, 168, 212 F

[56] References Cited

U.S. PATENT DOCUMENTS

| | | | |
|---|---|---|---|
| 3,841,987 | 10/1974 | Friese et al. | 204/195 S |
| 3,886,785 | 6/1975 | Stadler et al. | 73/23 |
| 3,891,529 | 6/1975 | Beesch | 204/195 S |
| 3,932,246 | 1/1976 | Stadler et al. | 73/27 R |
| 3,978,006 | 8/1976 | Topp et al. | 204/195 S |
| 4,001,758 | 1/1977 | Esper et al. | 73/27 R |
| 4,019,974 | 4/1977 | Weyl et al. | 204/195 S |
| 4,057,477 | 11/1977 | Weyl et al. | 204/195 S |
| 4,098,653 | 7/1978 | Kita et al. | 204/195 S |
| 4,127,464 | 11/1978 | Ichikawa et al. | 204/195 S |

Primary Examiner—Stephen A. Kreitman
Attorney, Agent, or Firm—William E. Johnson; Olin B. Johnson

[57] ABSTRACT

An improved oxygen sensor of the type adapted for installation in the exhaust conduit of an internal combustion engine. The improved sensor uses a metal oxide element to sense the partial pressure of oxygen in the exhaust gases to which the sensor is exposed. The sensor has a steel body and a ceramic member which extends into the exhaust gases to permit the exhaust gases to produce variations in an electrical characteristic of one of the sensor components. The improved sensor has a perforated protection tube that has a radially extending flange. The flange is located between the steel body and the ceramic member, which forms a seal preventing exhaust gases from inside the engine's exhaust conduit from leaking beyond the sensor to the atmosphere.

2 Claims, 4 Drawing Figures

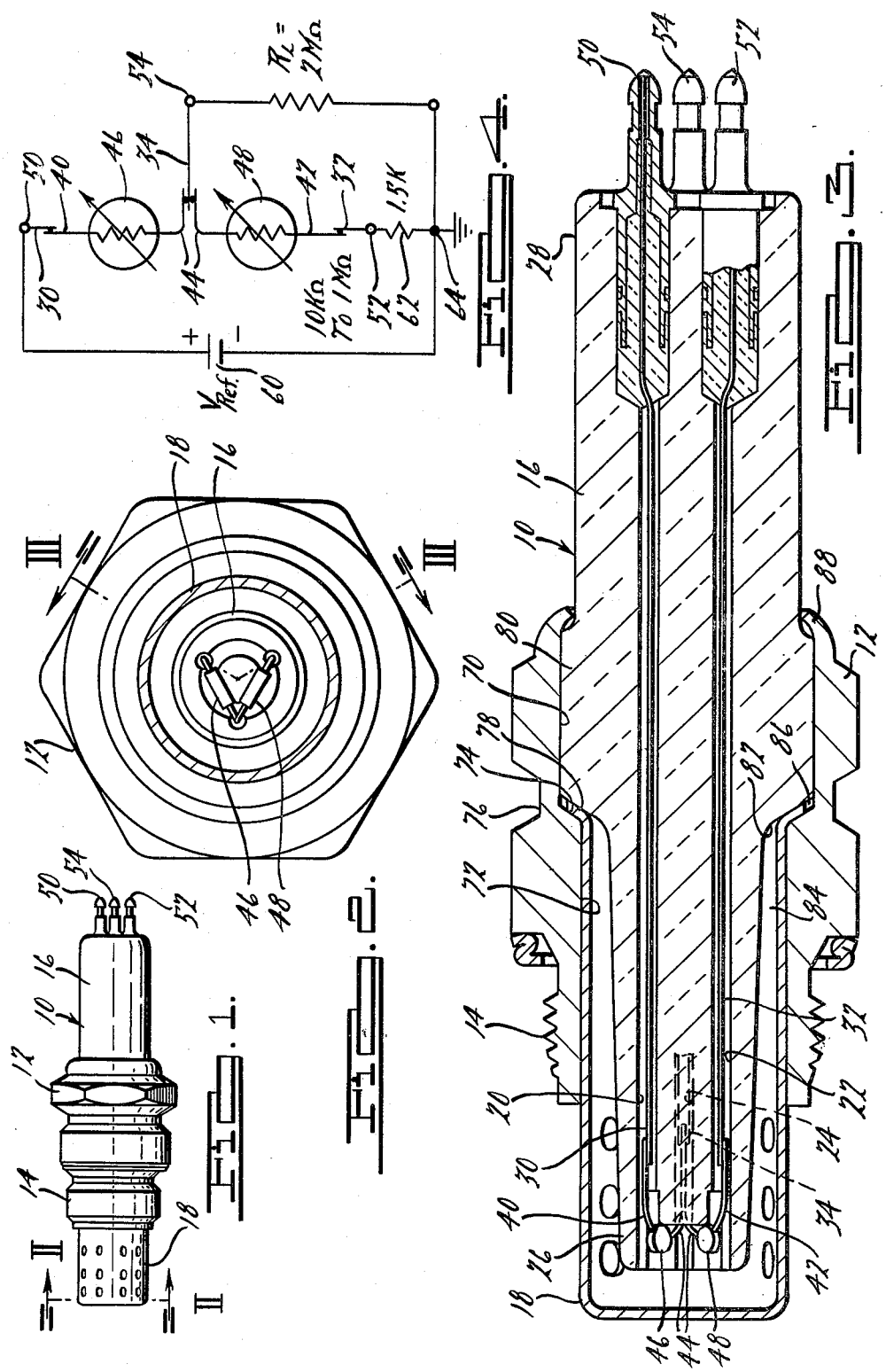

EXHAUST GAS SENSOR SEAL AND PROTECTION TUBE ARRANGEMENT

This is a continuation of application Ser. No. 5,423, filed Jan. 22, 1979, now abandoned.

BACKGROUND OF THE INVENTION

This invention relates to an improved exhaust gas oxygen sensor of the type adapted for installation in a conduit for conveying exhaust gases from an internal combustion engine. The improved sensor is responsive to the partial pressure of oxygen in the exhaust gases to which the sensor is exposed and has an electrical characteristic which varies, when the sensor is at operating temperatures in the range from about 350° C. to about 850° C., with the partial pressure of oxygen in the exhaust gases.

Exhaust gas sensors have been fabricated using either a ceramic zirconia tube or a titania oxygen sensing element of disc shape, the latter having electrode wires in embedded in the titania disc. Both sensor types convey to an electronic control system information concerning variations in an electrical characteristic of the oxygen sensing element as the composition of the exhaust gases from an internal combustion engine is varied. In the case of titania sensor, electrical lead wires and the titania oxygen sensing element are supported by a ceramic member mounted within a steel body that in use is attached to the exhaust conduit of an engine. The sensor is subjected to exhaust gases of varying composition, and a consequentially varying electrical signal passes from the sensing element to terminal pins at the end of the ceramic member. It has been found necessary with the exhaust gas sensor of this design to provide a seal between the steel body and the ceramic member and also to provide a perforated protection tube that surrounds the portion of the ceramic member designed to project into the exhaust conduit.

Protection tubes for exhaust gas oxygen sensor devices are known, as may be seen for example in commonly assigned U.S. Pat. No. 4,001,758 issued Jan. 4, 1977 to M. J. Esper, W. L. Green, S. R. Merchant and C. M. Wells, one of the present inventors. The above-mentioned patent relates to a titania exhaust gas sensor. Other sensor types are known as is evidenced by the following U.S. Pat. Nos. issued to Robert Bosch GmbH of Stuttgart, Germany: 3,891,529 issued June 24, 1975 to O. Beesch; 3,841,987 issued Oct. 15, 1974 to K. H. Friese et al; and 3,978,006 issued Aug. 31, 1976 to B. Topp et al. These patents of Robert Bosch GmbH illustrate various designs and arrangements for exhaust gas sensors of the zirconia type. U.S. Pat. No. 3,891,529 illustrates a protection tube used in connection with a zirconia ceramic member and the sealing arrangement achieved between the protection tube and the zirconia member, which in this type of device is responsive to the partial pressure of oxygen. It should be noted that the zirconia sensors apply a tubular element which must be sealed on one side from the exhaust gases which on the other side must be subjected thereto. The side of the zirconia sealed from the exhaust gases is supplied with a reference gas, usually with air, and the exhaust sensor output electrical signal is obtained as an EMF generated across platinum electrode material applied on opposite sides of the zirconia tube to hold a platinum surface on its exterior in electrical contact with the steel body or with the protection tube surrounding the zirconia tube. Spring pressure may be used for this purpose.

SUMMARY OF THE INVENTION

In accordance with the present invention, an exhaust gas oxygen sensor has a ceramic member that has a projecting portion adapted to extend into the exhaust conduit of an internal combustion engine. The sensor is improved by the use of a protection tube that not only surrounds the projecting portion of the ceramic member, but that also has a radially extending flange which is located within the steel body of the sensor and which is compressed between the body and the ceramic member to provide a seal to prevent leakage of exhaust gases.

More specifically, in accordance with the invention, the exhaust gas sensor has a body adapted for connection to the exhaust conduit of an internal combustion engine. The body has an axial bore extending through it and has at least two portions of different bore diameter each extending over a length of the body bore. The body bore has a transition surface extending between the two diameters thereof, the larger diameter portion of the body having an end suitable for crimping in a radially inward direction.

A ceramic member has a projecting portion adapted to extend into the exhaust conduit. A central portion also is provided, and the ceramic member is of generally circular cross-section along its length. The central portion of the ceramic member is of diameter greater than the diameter of its projecting portion. The central portion of the ceramic member is received within the larger bore-diameter portion of the body such that the projecting portion is adapted to extend into an exhaust conduit when the body is installed therein as adapted for this purpose. The projecting portion of the ceramic member extends axially beyond the smaller bore-diameter portion of the body.

A cylindrical metal protection tube has perforations in it to permit exhaust gases to enter and has a flange extending in a radially outward direction. The protection tube is received within the smaller bore-diameter portion of the body and surrounds the projecting portions of the ceramic member. The flange of the protection tube is located adjacent the transition surface of the body bore and is contacted by a mating portion of the ceramic member.

In order to provide a force to achieve a sealing relationship between the radially extending flange of the protection tube and the body and ceramic member by which it is contacted on opposite sides, the end of the larger bore-diameter portion of the body is crimped. This produces a clamping force between the body and the ceramic member. This force acts upon the flange of the protection tube, thereby, to produce a seal that prevents flow of exhaust gases from the region in the protection tube between it and the projecting portion of the ceramic member. This flow of exhaust gases would take place through the area between the ceramic member and the central portion of the body in the absence of the seal formed in accordance with the invention.

From the above, it is apparent that the protection tube not only protects the ceramic member, but also acts to form a seal between the ceramic member and the steel body. This eliminates sealing rings previously required for this purpose.

The invention may be better understood by reference to the detailed description which follows and to the drawings.

BRIEF DESCRIPTION OF THE DRAWINGS

FIG. 1 is an elevational view of a titania exhaust gas oxygen sensor suitable for installation in the intake manifold of an internal combustion engine;

FIG. 2 is a sectional end view, taken along the line II—II in FIG. 1, and is shown in enlarged scale;

FIG. 3, is a sectional view, taken along the line III—III in FIG. 2, showing the internal structure of the sensor of FIGS. 1 and 2 also on an enlarged scale; and FIG. 4 is a circuit diagram illustrating the manner in which the titania oxygen sensing element and the termistor shown in FIGS. 1 through 3 are electrically connected with circuitry designed to receive the sensor output voltage.

DETAILED DESCRIPTION

With particular reference now to FIGS. 1 through 3, wherein like numerals refer to like parts in the several views, there is shown a complete titania exhaust gas sensor assembly generally designated by the numeral 10. The sensor 10 includes a steel body 12, which may be substantially identical to a commercially available spark plug body, having a threaded portion 14 for engagement with a suitably threaded aperture provided within the exhaust system of an internal combustion engine (not shown). In most cases, the sensor 10 would be installed in an aperture at a location in the exhaust manifold or conduit near the flange that would connect to an exhaust pipe. A ceramic member or insulator 16 of generally circular cross-section extends through the body 12 and has a tapered portion 26 projecting outwardly from the body 12 into the volume defined by the boundaries of a perforated shield or protection tube 18. The projecting portion 26 of the ceramic insulator, among other things, acts as a support structure for an oxygen sensing element 46 and a thermistor 48. There are three longitudinal passages 20, 22 and 24 extending from the projecting end 26 of the ceramic insulator to its opposite terminal portion or end 28. Wires 30, 32 and 34 are located in the respectively corresponding passages 20, 22 and 24 and are of a heat resistant character, preferably being made from an alloy such as 80% nickel-20% chromium wire. These electrically conductive wires are welded to precious-metal wire leads 40, 42 and 44, which are embedded in the disc-shaped ceramic, metal-oxide oxygen sensing and thermistor elements 46 and 48.

Element 46 is a ceramic titania $O_2$ sensor responsive to the partial pressure of oxygen in the gaseous medium to which this element is exposed. Sensor element 46 may be fabricated in accordance with the teachings of commonly assigned U.S. Pat. Nos. 3,886,785 issued June 3, 1975 and 3,932,246 issued Jan. 13, 1976, both in the names of Stadler et al. With regard to the fabrication of the oxygen sensing element 46, it is suggested that consideration be given to the teachings of commonly-assigned and previously or concurrently-filed patents, relating to exhaust gas sensors or thermistors, expected to issue subsequent to the filing date of this patent application.

The element 48 is a thermistor. The thermistor may be made from titania ceramic material of greater density, near its theoretical density, than the density of the porous titania oxygen sensor 46. Alternatively, the thermistor 48 may be constructed in accordance with the teachings of copending and commonly assigned U.S. patent application Ser. No. 857,498 filed Dec. 5, 1977 in the names of Logothetis, Laud and Park and entitled "Rare Earth-Yttrium, Transition Metal Oxide Thermistors". The thermistor 48 is intended to provide temperature compensation in accordance with the circuitry illustrated in FIG. 4 and is intended to be substantially nonresponsive to variations in the partial pressure of oxygen in the gaseous medium to which it is exposed.

The sensor of FIGS. 1 through 3 is intended to be used in conjunction with electronic circuitry for closed-loop feedback control of the amount of fuel supplied to an internal combustion engine. The sensor indicates whether the exhaust gases contain a substantial amount of HC and CO or whether instead there is a substantial amount of $CO_2$, $H_2O$ and $O_2$, thereby, indicating whether or not the air/fuel ratio of the mixture supplied to the engine was rich to lean with respect to the stoichiometric value of about 14.7 parts of air to each part of fuel by weight. This air/fuel ratio typically is expressed as a normalized air/fuel ratio lambda, wherein the actual ratio is divided by the stoichiometric value and the stoichiometric ratio therefore is represented as 1.0 in accordance with well known practice.

The ceramic metal oxide elements 46 and 48 operate over a temperature range extending from about 350° C. to 850° C. These elevated temperatures are produced primarily as a result of the location of the exhaust gas oxygen sensor 10 in the exhaust stream of an internal combustion engine. The sensor, therefore, is subjected repeatedly to wide variations in temperature. When installed in a motor vehicle, the sensor 10 may be subjected to environmental temperatures as low as −40° C. When the vehicle is placed in operation, this temperature may rise to 500° or 600° C. in a very short time. Cyclical heating and cooling of the sensor 10 may occur several times each day in typical motor vehicle usage.

In prior art titania exhaust gas sensor designs, there was a need to utilize one or more rings of material to achieve a seal between the body portion of exhaust gas sensor and its associated ceramic member or insulator, as is shown in the aforementioned U.S. Pat. No. 4,001,758. In sensors of this type, the seal prevents exhaust gases within the protection tube from flowing, through the space between the body and the ceramic member, to the atmosphere.

The present invention is an improvement over the seal and protection tube arrangement of prior art exhaust gas sensors having ceramic members mounted within steel bodies. According to the invention, the protection tube 18, which in previous designs would have been welded to the body 12, is provided with a flange which not only serves to retain the protection tube in its proper position, but which also serves to provide a deformable sealing material between the body 12 and the ceramic member 16. This eliminates any requirements for a separate sealing material or component.

The preferred design of the exhaust gas oxygen sensor improved protection tube and sealing arrangement is best shown in FIG. 3. The sensor body 12 has an axially-extending bore of varying diameter in which the protection tube 18 and ceramic insulator 16 are positioned in cooperative relationship. The bore in the body has a larger-diameter portion 70, a smaller-diameter portion 72 and a portion 74 forming a transition surface extending between the larger and smaller diameter portions of the bore. On the exterior portion of the body, a groove 76 is provided in a location adjacent the transition surface of the bore. Because the seal between the body 12 and the ceramic member 16 is formed in the area of the bore transition, the groove aids in removing heat from the seal region due to the reduction in body material at this location. The seal is effected with the use of a radially-extending flange 78 that is provided on the protection tube 18.

The central portion 80 of the ceramic member 16 is received by the body 12 in its portion 70 having the larger bore diameter. Located between the transition surface of the bore in body 12 and the mating surface 82 of the ceramic member is the flange 78 of the protection tube 18. The direct contact of the body and the mating portion of the ceramic member with the flange maintains a clamping force on the flange which forms a seal. This prevents exhaust gases within the area 84, between the protection tube and the projecting portion of the ceramic member, and also between the protection tube and the body, from flowing through the area between the ceramic member central portion 80 and the body 12. During assembly of the exhaust gas oxygen sensor, the flange 78 is clamped between the body and ceramic member as shown. The end portion 88 of the body larger bore-diameter portion is crimped radially inwardly over the central portion of the ceramic member to maintain the axial clamping force on the flange. This produces some deformation of the protection tube flange in conformity with the surfaces it contacts. The protection tube may be fabricated from SAE type 310 stainless steel having a thickness of 0.5 mm. Ceramic material conventionally used to form spark plug insulators may be used in fabricating the ceramic member 16 used in the illustrated titania exhaust gas sensor. A space 86 between these components and the steel body 12 accommodates the deformation of the protection tube flange.

The exhaust gas sensor 10 has terminals 50, 52 and 54 designed for connection to external circuitry as specified above to enable it to be used in a feedback fuel control system. With particular reference now to FIG. 4, there is shown a circuit that schematically represents the manner in which the sensor 10 is utilized in association with such external circuitry. A DC source of regulated reference voltage 60 has its positive terminal connected to terminal 50 of the sensor oxygen responsive element 46. The lead wires 40, 42 and 44 from the sensor 46 and thermistor 48 are welded or otherwise joined. Respectively, to lead wires 30, 32 and 34 to interconnect the two ceramic elements 46 and 48 as shown. The thermistor element 48 is connected through a responsive shaping resistor 62 to ground potential at 64. The output voltage of the sensor 10 is taken between the sensor terminal 54 and ground potential. This signal is applied across the input impedance or load resistance $R_L$ (about two megohms) of the engine control electronic circuitry.

The input voltage to the circuit of FIG. 4 is obtained from the source reference 60 and is applied across the voltage divider comprising the series-connected variable resistances of oxygen sensor 46 and thermistor 48 in series with the response-shaping resistor 62. The output voltage is taken across the load resistance $R_L$.

The resistance values of both the oxygen sensor 46 and the thermistor 48 vary as a function of temperature and in the same direction, that is, the resistance of these elements decreases with increasing temperature. As a result, the voltage dividing effect provides an output voltage across the load resistance $R_L$ that is independent of temperature. The oxygen sensor 46, however, has a resistance which varies not only with temperature but also with the partial pressure of oxygen in the gaseous medium to which the sensor is exposed. An increase in the resistance of the oxygen sensor 46 causes the output voltage across the load $R_L$ to decrease, and a reduction in the resistance of the oxygen sensor causes a corresponding increase in the output voltage across the resistance $R_L$. Otherwise stated, an increase in oxygen content in the gaseous medium surrounding the oxygen sensing device 46 causes its resistance to increase and thereby causes a reduction in the voltage across the load resistance $R_L$. A decrease in the oxygen content of the gaseous medium causes the resistance of the oxygen sensor 46 to decrease in a corresponding manner and this causes an increase in the voltage across the load resistance $R_L$.

Based upon the foregoing description of the invention, what is claimed is:

1. A titania exhaust gas oxygen sensor of the type adapted for installation in a conduit for conveying exhaust gases from an internal combustion engine, the sensor having a body made from a metal material, the body having an axial bore through it, external threads coaxial with the bore and at one end of the body, the body also having a hexagonal exterior portion suitable for engagement by a tool for turning the body, the sensor having a ceramic member received within the bore in the body and the body having means for effecting an axial force acting to form a seal between the ceramic member and the body, and a protection tube received within the bore in the body, the protection tube having a flange positioned between the body and the ceramic member and cooperating with the body and the ceramic member in forming the seal between them, the exhaust gas oxygen sensor being characterized by: a groove in the exterior of the body, the groove being positioned adjacent the seal formed by the body, the flange of the protection tube and the ceramic member, and the groove being separated from the threads on the exterior of the body by the hexagonal exterior portion thereof.

2. An improved titania exhaust gas oxygen sensor of the type adapted for installation in a conduit for conveying exhaust gases from an internal combustion engine and for use in conjunction with electronic circuitry for closed-loop feedback control of the amount of fuel supplied in the internal combustion engine, the improved sensor having a ceramic titania oxygen sensing component responsive to the partial pressure of oxygen in the exhaust gases to which the sensor is exposed, the component having an electrical characteristic which varies when at operating temperatures in the range from about 350° C. to about 850° C. with the partial pressure of oxygen in the exhaust gases, the improved sensor also having a thermistor and three electrically conductive, heat resistant wires coupled to the oxygen sensing component and the thermistor, the sensor comprising:

a steel body adapted for connection to the exhaust conduit of an the internal combustion engine, the body having an axial bore extending through it, the body bore having at least two portions of different bore diameter and the body bore having a transition surface extending between the diameters thereof, the larger diameter portion of the body bore having an end thereof suitable for crimping in a radially inward direction, the small diameter portion having a threaded portion for engagement with a suitably threaded aperture provided within the exhaust system of the internal combustion engine;

a ceramic member having a projecting portion, adapted to extend into the exhaust conduit, and a central portion, the ceramic member insulator being of generally circular cross-section along its length, the central portion being of diameter greater than the diameter of the projecting portion, the central portion being received within the larger bore diameter portion of the body such that the projecting portion is adapted to project into an exhaust conduit when the body is installed therein as adapted therefor, the projecting portion of the ceramic member extending axially beyond the smaller bore diameter portion of the body and acting as a support structure for the oxygen sensing element and the thermistor;

said ceramic member including three longitudinal passages extending between the two axial ends of said ceramic member for passing the wires connecting to the oxygen sensing component and thermistor;

a cylindrical metal protection tube having perforations therein to permit exhaust gases to enter and having a flange extending in a radially outward direction to provide a deformable sealing material, the protection tube being received within the smaller bore diameter portion of the body and surrounding the projecting portion of the ceramic member extending beyond the body, said flange of the protection tube being located adjacent the transition surface of the body bore and being contacted by a mating portion of the ceramic member, the larger bore diameter portion of the body being crimped at its end into contact with the ceramic member to produce a clamping force between the body and the ceramic member acting upon said flange of the protection tube, thereby, to produce a seal that prevents flow of exhaust gases from the region in the protection tube between it and the projecting portion of the ceramic member through the area between the ceramic member central portion and the body;

said flange of the protection tube being in direct contact on its exterior side with the transition surface of the body bore, wherein the interior portion of the flange of the protection tube is in contact with a mating portion of the ceramic member, and wherein a space is provided between the body and the flange of the protection tube to permit some deformation of the flange when a force is applied to the body and the ceramic member during crimping of the body portion; and said body having an external groove adjacent the seal formed between the body, the flange of the protection tube and the ceramic member.

* * * * *